United States Patent
Zan et al.

(10) Patent No.: US 11,041,822 B2
(45) Date of Patent: Jun. 22, 2021

(54) SENSING ELEMENT

(71) Applicant: E Ink Holdings Inc., Hsinchu (TW)

(72) Inventors: Hsiao-Wen Zan, Hsinchu (TW);
Chuang-Chuang Tsai, Hsinchu (TW);
Yu-Nung Mao, Hsinchu (TW);
Hung-Chuan Liu, Hsinchu (TW);
Zong-Xuan Li, Hsinchu (TW);
Wei-Tsung Chen, Hsinchu (TW)

(73) Assignee: E Ink Holdings Inc., Hsinchu (TW)

( * ) Notice: Subject to any disclaimer, the term of this patent is extended or adjusted under 35 U.S.C. 154(b) by 0 days.

(21) Appl. No.: 16/109,733

(22) Filed: Aug. 22, 2018

(65) Prior Publication Data

US 2019/0079040 A1    Mar. 14, 2019

(30) Foreign Application Priority Data

Sep. 12, 2017    (TW) ................................ 106131287

(51) Int. Cl.
    *G01N 27/12*        (2006.01)
    *G01N 33/483*      (2006.01)

(52) U.S. Cl.
    CPC ......... *G01N 27/126* (2013.01); *G01N 27/127* (2013.01); *G01N 33/483* (2013.01)

(58) Field of Classification Search
None
See application file for complete search history.

(56) References Cited

U.S. PATENT DOCUMENTS

| | | | |
|---|---|---|---|
| 5,477,716 A | 12/1995 | Snow | |
| 7,081,368 B2* | 7/2006 | Hiramoto | G01N 25/56 |
| | | | 257/440 |
| 8,421,483 B2 | 4/2013 | Klinghult et al. | |
| 8,829,767 B2 | 9/2014 | Wang et al. | |
| 2006/0249382 A1 | 11/2006 | Hengstenberg et al. | |
| 2007/0040165 A1 | 2/2007 | Dimmler et al. | |
| 2010/0163410 A1 | 7/2010 | Mastromatteo et al. | |
| 2011/0091510 A1* | 4/2011 | Lele | B82Y 30/00 |
| | | | 424/400 |
| 2011/0132449 A1* | 6/2011 | Ramadas | H05B 33/04 |
| | | | 136/256 |
| 2012/0086431 A1 | 4/2012 | Zan et al. | |

(Continued)

FOREIGN PATENT DOCUMENTS

| | | |
|---|---|---|
| CN | 102257384 A | 11/2011 |
| CN | 104849317 A | 8/2015 |

(Continued)

OTHER PUBLICATIONS

Corresponding Taiwan office action dated Apr. 30, 2018.

(Continued)

*Primary Examiner* — Noam Reisner
(74) *Attorney, Agent, or Firm* — CKC & Partners Co., LLC

(57) ABSTRACT

A sensing element includes a conductive substrate, a zinc oxide seed layer, a plurality of zinc oxide nanorods, a film with an electrical double layer, and an organic sensing layer. The zinc oxide seed layer is located on the conductive substrate. The zinc oxide nanorods extend from the zinc oxide seed layer. The film with the electrical double layer covers the zinc oxide nanorods. The organic sensing layer is located on the film with the electrical double layer.

9 Claims, 4 Drawing Sheets

(56) References Cited

U.S. PATENT DOCUMENTS

| | | | |
|---|---|---|---|
| 2012/0164434 A1* | 6/2012 | Ramadas | H01L 51/5253 |
| | | | 428/328 |
| 2012/0223370 A1 | 9/2012 | Zan et al. | |
| 2013/0071289 A1 | 3/2013 | Knoll | |
| 2013/0149844 A1 | 6/2013 | Kim et al. | |
| 2013/0269766 A1 | 10/2013 | Park et al. | |
| 2014/0333184 A1 | 11/2014 | Wang et al. | |
| 2016/0056324 A1 | 2/2016 | Feinstein | |
| 2016/0162104 A1 | 6/2016 | Kim et al. | |
| 2020/0168822 A1* | 5/2020 | Roqan | H01L 31/03926 |

FOREIGN PATENT DOCUMENTS

| | | |
|---|---|---|
| KR | 20030025037 A | 3/2003 |
| TW | 201602031 A | 1/2016 |
| TW | 201603143 A | 1/2016 |
| TW | 201708813 A | 3/2017 |

OTHER PUBLICATIONS

James S. Lee et al., "Highly Sensitive and Multifunctional Tactile Sensor Using Free-standing ZnO/ PVDF Thin Film with Graphene Electrodes for Pressure and Temperature Monitoring", Scientific Reports, 2015.

H. Ghayour et al., "The effect of seed layer thickness on alignment and morphology of ZnO nanorods", Vacuum, 2011.

Hsiao-Wen Zan et al., "Room-temperature-operated sensitive hybrid gas sensor based on amorphous indium gallium zinc oxide thin-film transistors", Applied Physics Letters, 2011.

Corresponding China office action dated Oct. 26, 2020.

* cited by examiner

SENSING ELEMENT

CROSS-REFERENCE TO RELATED APPLICATION

This application claims priority to Taiwan Application Serial Number 106131287, filed Sep. 12, 2017, which is herein incorporated by reference.

BACKGROUND

Field of Invention

The present invention relates to a sensing element. More particularly, the present invention relates to a sensing element including a film with an electrical double layer.

Description of Related Art

In recent years, nanotechnology develops rapidly. Various nanomaterials have been widely applied in various technical fields. For example, nano metal oxide materials can be used for fabricating a gas sensor. However, the fabrication process of using nano metal oxide materials to fabricate a gas sensor is usually complex and hard. Moreover, the surface of the gas sensor fabricated by the nano metal oxide materials is usually uneven, and therefore adversely influences the service life of the gas sensor.

In view of the above, a new sensor is necessary to solve the above problems.

SUMMARY

The present disclosure provides a sensing element including a conductive substrate, a zinc oxide seed layer, a plurality of zinc oxide nanorods, a film with an electrical double layer, and an organic sensing layer. The zinc oxide seed layer is located on the conductive substrate. The zinc oxide nanorods extend from the zinc oxide seed layer. The film with the electrical double layer covers the zinc oxide nanorods. The organic sensing layer is located on the film with the electrical double layer.

In some embodiments, the zinc oxide nanorods are embedded in the film with the electrical double layer.

In some embodiments, the film with the electrical double layer fills a gap between the zinc oxide nanorods.

In some embodiments, the zinc oxide nanorods are separated from the organic sensing layer by the film with the electrical double layer.

In some embodiments, the sensing element further includes a resistance measuring element, wherein the resistance measuring element electrically connects the conductive substrate.

In some embodiments, an interface between the film with the electrical double layer and the organic sensing layer is substantially planar.

In some embodiments, the film with the electrical double layer has a substantially planar upper surface.

In some embodiments, the organic sensing layer has a substantially planar upper surface.

In some embodiments, a material of the film with the electrical double layer comprises a fluorine-containing polymer.

In some embodiments, the organic sensing layer comprises at least one antigen.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
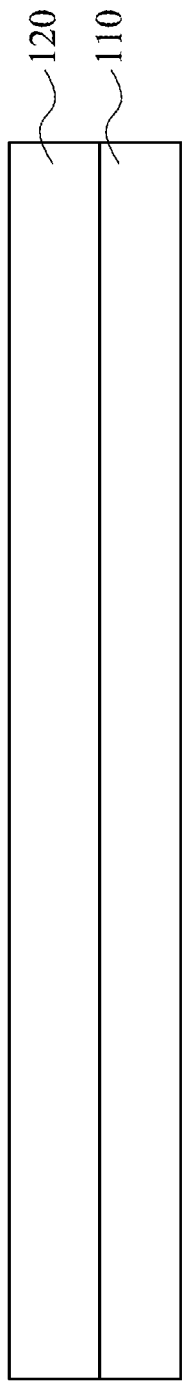
FIGS. 1-4 are cross-sectional views of a sensing element at various fabrication stages according to various embodiments.

Reference will now be made in detail to the present embodiments of the invention, examples of which are illustrated in the accompanying drawings. Wherever possible, the same reference numbers are used in the drawings and the description to refer to the same or like parts.

The following embodiments are disclosed with accompanying diagrams for detailed description. For illustration clarity, many details of practice are explained in the following descriptions. However, it should be understood that these details of practice do not intend to limit the present disclosure. That is, these details of practice are not necessary in parts of embodiments of the present disclosure. Furthermore, for simplifying the drawings, some of the conventional structures and elements are shown with schematic illustrations.

The present disclosure provides a sensing element. FIGS. 1-4 are cross-sectional views of a sensing element at various fabrication stages according to various embodiments.

Please refer to FIG. 1. A metal oxide seed layer, such as a zinc oxide seed layer 120, is formed on a conductive substrate 110. The zinc oxide seed layer 120 is beneficial to subsequent growth of zinc oxide nanorods. In some embodiments, the zinc oxide seed layer 120 is in direct contact with the conductive substrate 110. The method of forming the zinc oxide seed layer 120 includes but not limited to electrophoretic deposition (EPD), sol-gel method, spin coating, e-gun evaporation, chemical vapor deposition (CVD), pulsed laser deposition (PLD), atomic layer deposition (ALD), or sputtering. CVD, for example, is metal-organic chemical vapor deposition (MOCVD).

In some embodiments, a material of the conductive substrate 110 includes metal, alloy, metal oxide, or a combination thereof. For example, the material of the conductive substrate 110 includes but not limited to indium tin oxide (ITO). In some embodiments, the conductive substrate 110 is ITO substrate. The zinc oxide seed layer 120 can be directly formed on the ITO substrate by electrophoretic deposition or sol-gel method.

Figure 2:
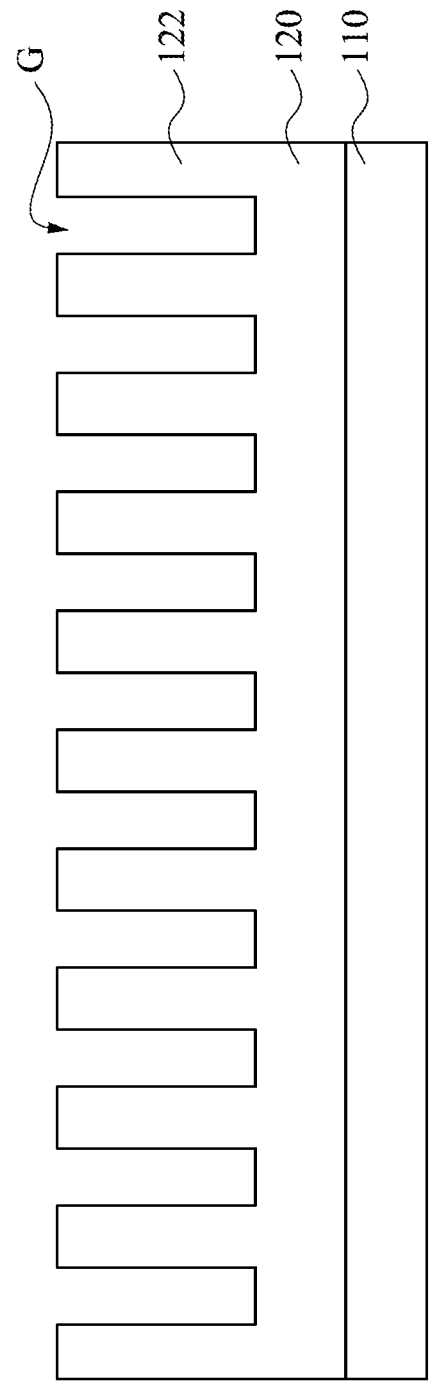

Please refer to FIG. 2. Metal oxide nanorods, such as zinc oxide nanorods 122, are formed on the zinc oxide seed layer 120. The method of forming the zinc oxide nanorods 122 includes but not limited to hydrothermal method, chemical vapor deposition (for example, metal-organic chemical vapor deposition), pulsed laser deposition, molecular beam epitaxy (MBE), or electrophoretic deposition. For example, by electrophoretic deposition, the zinc oxide nanorods 122 can be formed on the zinc oxide seed layer 120 through self-assembly of zinc oxide.

The arrangement of the zinc oxide nanorods 122 shown in FIG. 2 is illustrative. According to different methods of forming the zinc oxide nanorods 122, in some embodiments, oriented zinc oxide nanorods 122 are grown on the zinc oxide seed layer 120. Therefore, the zinc oxide nanorods 122 arrange regularly. In some other embodiments, non-oriented zinc oxide nanorods 122 are grown on the zinc oxide seed layer 120. Therefore, the zinc oxide nanorods arrange irregularly.

As shown in FIG. 2, the zinc oxide nanorods 122 are grown on the zinc oxide seed layer 120. Therefore, the zinc oxide nanorods 122 extend from the zinc oxide seed layer 120. In some embodiments, the structure constituted by the zinc oxide nanorods 122 is called zinc oxide nanorod array. In some embodiments, the zinc oxide nanorods 122 are called zinc oxide nanowires. Therefore, the structure constituted by the zinc oxide nanowires is called zinc oxide nanowire array. In some embodiments, the zinc oxide nanorods 122 include a dopant, such as lithium, magnesium, copper, aluminium, gallium, indium, or cobalt.

Figure 3:
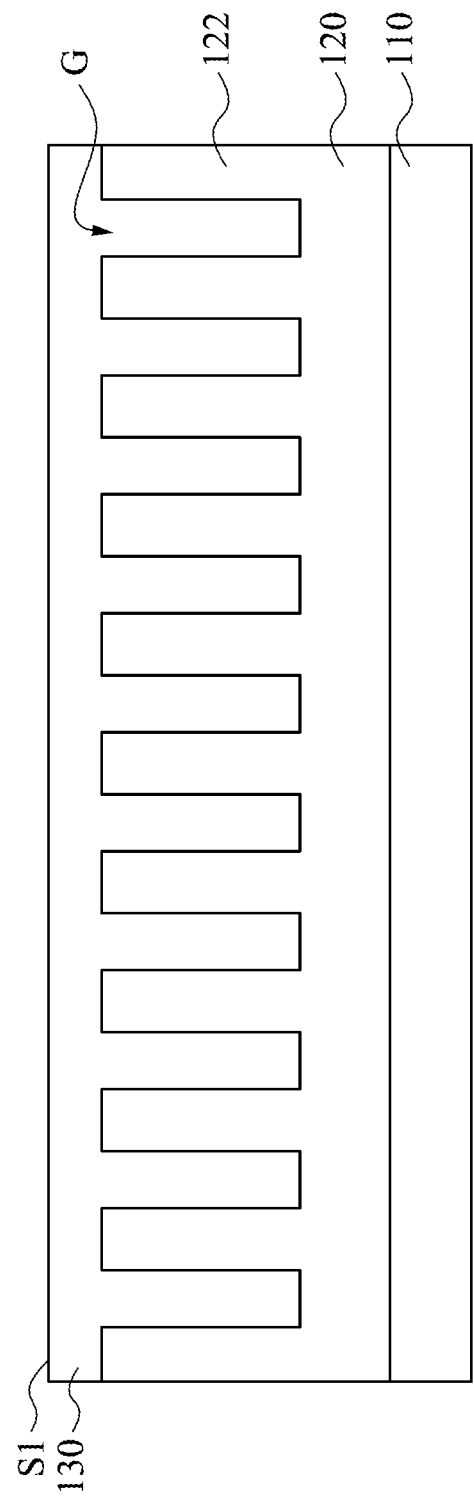

Please refer to FIG. 3. A film 130 with an electrical double layer is formed on the zinc oxide nanorods 122 to cover the zinc oxide nanorods 122. The film 130 with the electrical double layer can prevent degradation of the zinc oxide nanorods 122. In some embodiments, the zinc oxide nanorods 122 are embedded in the film 130 with the electrical double layer.

The term "the film with the electrical double layer" referred in the present disclosure is a film having an electrical double layer in its interior. "The film with the electrical double layer" can also be called "a film including electrical double layer" or "a film with an electrical double layer structure." More specifically, the interior of the film 130 with the electrical double layer has freely movable ions, and therefore the film 130 with the electrical double layer can generate an electrical double layer including a positive charge layer and a negative charge layer and has high permittivity. In some embodiments, a material of the film 130 with the electrical double layer includes a fluorine-containing polymer. The fluorine-containing polymer, for example, includes but not limited to polyvinylidene difluoride (PVDF), cyclic transparent optical polymer (CYTOP), or a combination thereof.

The method of forming the film 130 with the electrical double layer includes but not limited to liquid process. For example, the film 130 with the electrical double layer can directly cover the zinc oxide nanorods 122 by coating. Therefore, the film 130 with the electrical double layer is in direct contact with the zinc oxide nanorods 122. In some embodiments, the gaps G between the zinc oxide nanorods 122 are filled by the film 130 with the electrical double layer. In some embodiments, the film 130 with the electrical double layer has a substantially planar upper surface S1.

Figure 4:
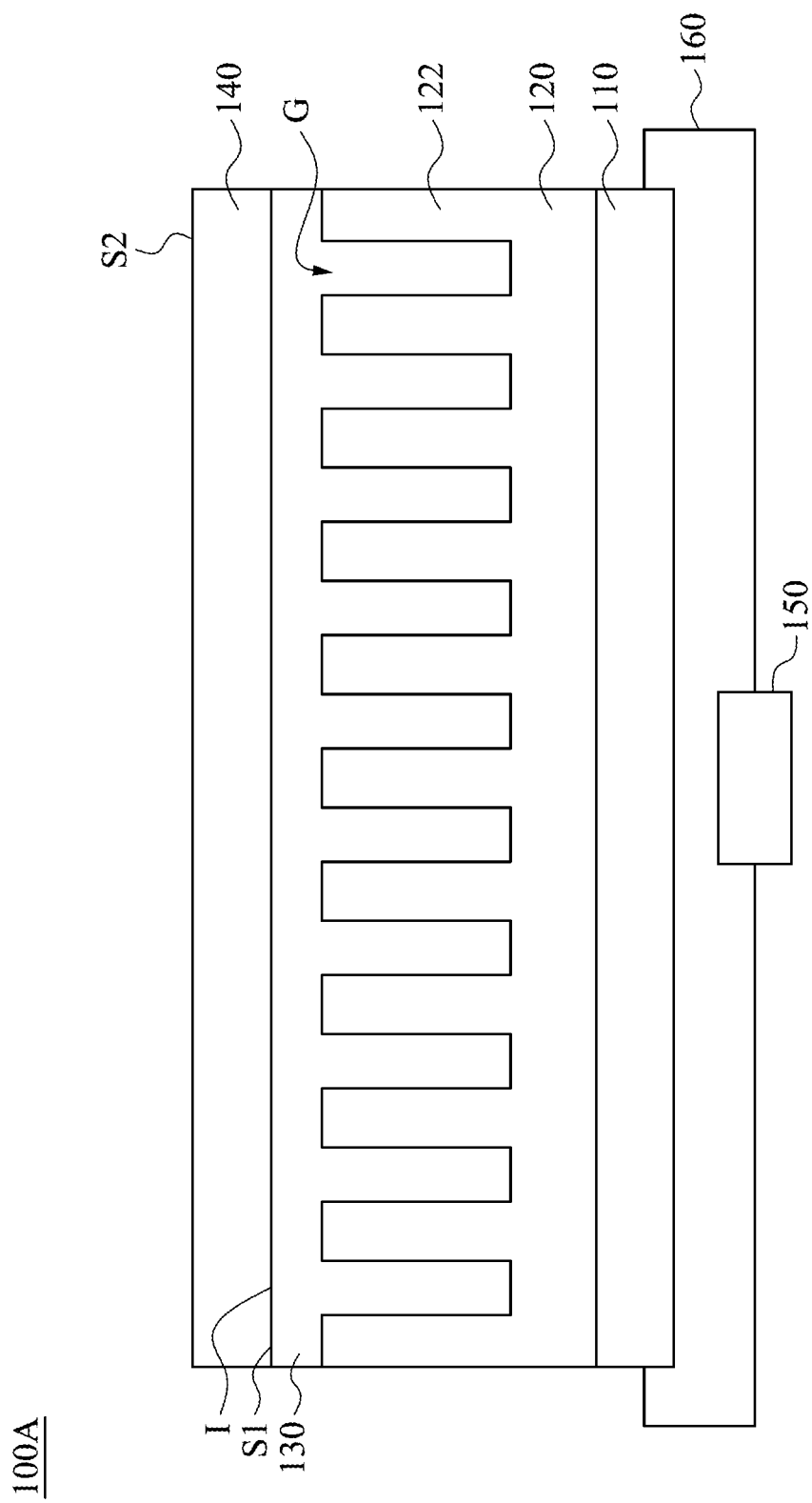

Please refer to FIG. 4. An organic sensing layer 140 is formed on the film 130 with the electrical double layer to form a sensing element 100A. The method of forming the organic sensing layer 140 includes but not limited to coating. The organic sensing layer 140 has an ability to absorb analytes or react with analytes. When the organic sensing layer 140 absorbs analytes or reacts with analytes, the energy barrier and the potential of the organic sensing layer 140 change accordingly. The material of the organic sensing layer 140 is determined by the species of analytes. The analytes may be gaseous, liquid, or solid. For example, the analytes include but not limited to carbon monoxide, oxygen gas, formaldehyde, ozone, hydrogen gas, acetylene, hexane, or antibody.

In some embodiments, the organic sensing layer 140 has a functional group that can react with an analyte. In some embodiments, the analyte is carboxylic acid, and the organic sensing layer has hydroxyl group (—OH). In some embodiments, the analyte is alcohol, and the organic sensing layer has carboxyl group (—COOH). In some embodiments, the analyte is amine, and the organic sensing layer has carboxyl group. In some embodiments, the analyte is amide, and the organic sensing layer has carboxyl group.

As shown in FIG. 4, the sensing element 100A includes the conductive substrate 110, the zinc oxide seed layer 120, the zinc oxide nanorods 122, the film 130 with the electrical double layer, and the organic sensing layer 140. The zinc oxide seed layer 120 is located on the conductive substrate 110. The zinc oxide nanorods 122 extend from the zinc oxide seed layer 120. The film 130 with the electrical double layer covers the zinc oxide nanorods 122. The organic sensing layer 140 is located on the film 130 with the electrical double layer. In some embodiments, the zinc oxide nanorods 122 are separated from the organic sensing layer 140 by the film 130 with the electrical double layer. In some embodiments, because the upper surface S1 of the film 130 with the electrical double layer is substantially planar, an interface I between the film 130 with the electrical double layer and the organic sensing layer 140 is also substantially planar. In some embodiments, the organic sensing layer 140 has a substantially planar upper surface S2. Therefore, the sensing element 100A is not easily damaged during sensing and therefore has longer service life.

In some embodiments, the sensing element 100A further includes a resistance measuring element 150, wherein the resistance measuring element 150 electrically connects the conductive substrate 110. For example, the resistance measuring element 150 may be ohmmeter or multimeter.

As shown in FIG. 4, the resistance measuring element 150 electrically connects the two ends of the conductive substrate 110 by wires 160 to measure the resistance of the conductive substrate 110, the zinc oxide seed layer 120, the zinc oxide nanorods 122, the film 130 with the electrical double layer, and the organic sensing layer 140.

When the organic sensing layer 140 absorbs analytes or reacts with analytes, the energy barrier and the potential of the organic sensing layer 140 change accordingly, thereby causing change of the charge distribution in the film 130 with the electrical double layer. Accordingly, the potential of the film 130 with the electrical double layer change, and therefore the resistance value measured by the resistance measuring element 150 change. The amount of the analytes can be known by the variation of the resistance value. In other words, the conductive substrate 110, the zinc oxide seed layer 120, the zinc oxide nanorods 122, the film 130 with the electrical double layer, and the organic sensing layer 140 can be seen as a variable resistance. Because the zinc oxide nanorods 122 have high surface area and the film 130 with the electrical double layer has high permittivity, the sensing element 100A of the present disclosure may have quite good sensitivity. In some other embodiments, the zinc oxide nanorods 122 can be replaced by other materials to achieve the object of increasing surface area in the present disclosure.

Figure 5:
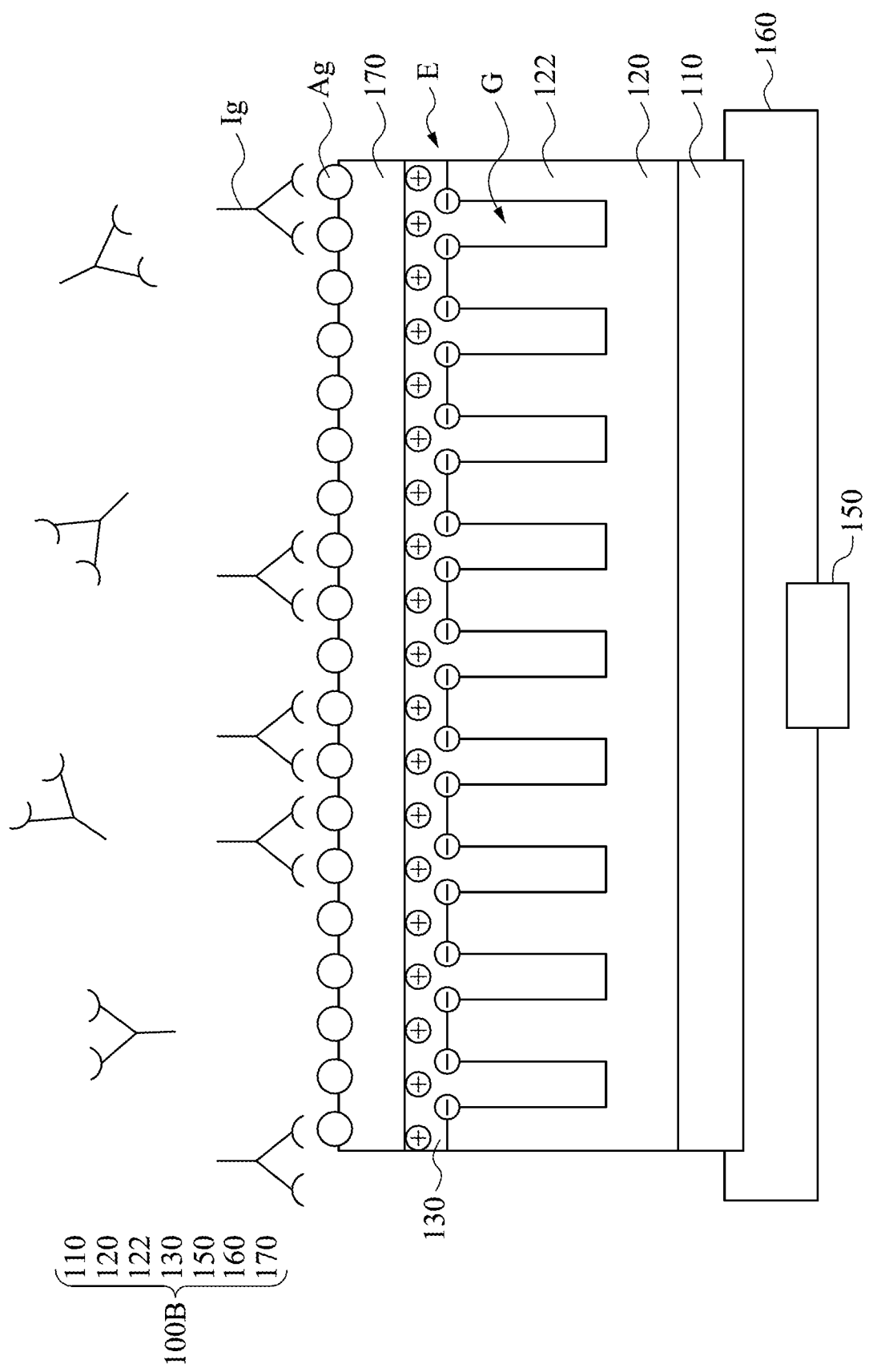
FIG. 5 is an illustration of a sensing element during sensing according to one embodiment.

Please refer to FIG. 5. FIG. 5 is an illustration of a sensing element 100B during sensing according to one embodiment. The sensing element 100B includes the conductive substrate 110, the zinc oxide seed layer 120, the zinc oxide nanorods 122, the film 130 with the electrical double layer, and an organic sensing layer 170. The organic sensing layer 170 includes at least one antigen Ag, and the analytes includes at least one antibody Ig.

The difference between the sensing element 100B of FIG. 5 and the sensing element 100A of FIG. 4 is that FIG. 5 further shows the organic sensing layer 170 has at least one antigen Ag which can combine with the antibody Ig and an electrical double layer E in the film 130 with the electrical double layer. It is noted that the electrical double layer E shown in FIG. 5 is illustrative and exemplary.

When one antigen Ag of the organic sensing layer 170 combines with one antibody Ig, the potential of the organic sensing layer 170 change accordingly, thereby causing change of the charge distribution in the film 130 with the electrical double layer. Accordingly, the potential of the film 130 with the electrical double layer change, and therefore the resistance value measured by the resistance measuring element 150 change. The amount of the antibodies Ig can be known by the variation of the resistance value.

In view of the foregoing, the present disclosure provides a sensing element including a film with an electrical double layer. The sensing element has advantages of high sensitivity, long service life, and preventing degradation of the zinc oxide nanorods.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A sensing element, comprising:
   a conductive substrate;
   a zinc oxide seed layer located on the conductive substrate and in direct contact with the conductive substrate;
   a plurality of zinc oxide nanorods extending from the zinc oxide seed layer, wherein the conductive substrate is electrically connected to the zinc oxide seed layer and the zinc oxide nanorods;
   a film with an electrical double layer covering the zinc oxide nanorods; and
   an organic sensing layer located on the film with the electrical double layer, wherein the organic sensing layer is seperated from the zinc oxide nanorods by the film with the electrical double layer.

2. The sensing element of claim 1, wherein the zinc oxide nanorods are embedded in the film with the electrical double layer.

3. The sensing element of claim 1, wherein the film with the electrical double layer fills a gap between the zinc oxide nanorods.

4. The sensing element of claim 1, further comprising a resistance measuring element, wherein the resistance measuring element electrically connects the conductive substrate.

5. The sensing element of claim 1, wherein an interface between the film with the electrical double layer and the organic sensing layer is substantially planar.

6. The sensing element of claim 1, wherein the film with the electrical double layer has a substantially planar upper surface.

7. The sensing element of claim 1, wherein the organic sensing layer has a substantially planar upper surface.

8. The sensing element of claim 1, wherein a material of the film with the electrical double layer comprises a fluorine-containing polymer.

9. The sensing element of claim 1, wherein the organic sensing layer comprises at least one antigen.

* * * * *